United States Patent
Psaros

Patent Number: 6,032,665
Date of Patent: Mar. 7, 2000

[54] DOSING DEVICE FOR ADDING AN ADDITIVE FLUID TO BREATHING GAS IN AN ANAESTHESIA MACHINE OR VENTILATOR

[75] Inventor: Georgios Psaros, Tullinge, Sweden

[73] Assignee: Siemens Elema AB, Solna, Sweden

[21] Appl. No.: 08/842,367

[22] Filed: Apr. 24, 1997

[30] Foreign Application Priority Data

May 6, 1996 [SE] Sweden ................................. 9601719

[51] Int. Cl.[7] ................................................ A61M 15/00
[52] U.S. Cl. ................................ 128/203.12; 128/203.14
[58] Field of Search ........................ 128/203.12, 203.19, 128/204.26, 205.24, 204.23, 203.14; 251/210; 73/861.04, 272 R, 275, 276; 222/14–16, 21, 71, 255; 261/DIG. 37; 604/151; 417/137, 144

[56] References Cited

U.S. PATENT DOCUMENTS

| | | | |
|---|---|---|---|
| 3,785,526 | 1/1974 | Shinn | 222/14 |
| 3,887,110 | 6/1975 | Porter | 222/16 |
| 3,894,536 | 7/1975 | Tysk | 128/203.12 |
| 4,364,386 | 12/1982 | Jenkins et al. | 604/131 |
| 4,819,629 | 4/1989 | Jonson | 128/204.23 |
| 4,895,500 | 1/1990 | Hök et al. | |
| 5,088,631 | 2/1992 | Torterotot | 222/389 |
| 5,385,540 | 1/1995 | Abbott et al. | 604/4 |
| 5,516,429 | 5/1996 | Snodgrass et al. | 210/767 |
| 5,531,680 | 7/1996 | Dumas et al. | 604/67 |
| 5,665,070 | 9/1997 | McPhee | 604/131 |
| 5,693,016 | 12/1997 | Gumaste et al. | 604/131 |
| 5,878,771 | 3/1999 | Mayeaux | 137/88 |

FOREIGN PATENT DOCUMENTS

| | | |
|---|---|---|
| 448 347 | 6/1987 | Sweden . |
| 2 253 353 | 9/1992 | United Kingdom . |

*Primary Examiner*—Aaron J. Lewis
*Attorney, Agent, or Firm*—Hill & Simpson

[57] ABSTRACT

A dosing device for adding small amounts of an additive gas or liquid, such as NO or liquid anaesthetic, to a breathing gas in an inspiratory line in an anaesthetic machine or ventilator, has a constant-volume dosing chamber with an inlet, equipped with a first valve, for connection to a source of gas or liquid supplying the additive gas or liquid at a predetermined, constant, positive pressure, and an outlet, equipped with a second valve, for injecting gas or liquid from the dosing chamber into breathing gas. Control elements are arranged to open and close the valves in a controlled fashion. A control unit is also arranged to cause the operating elements to open the second valve for one or a number of predetermined intervals during the inspiratory phase.

10 Claims, 3 Drawing Sheets

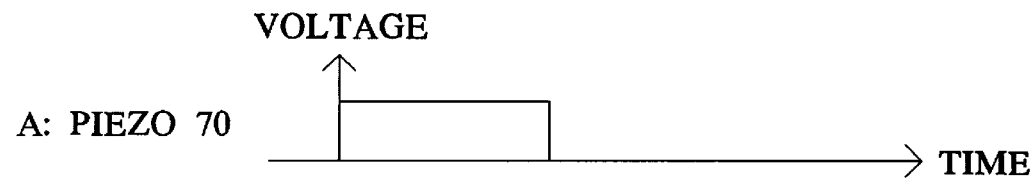
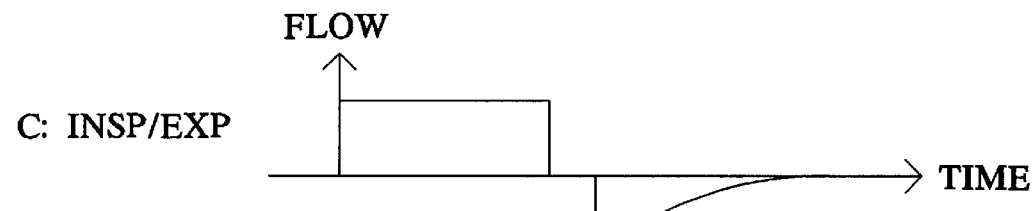
*FIG. 3*
*FIG. 4*
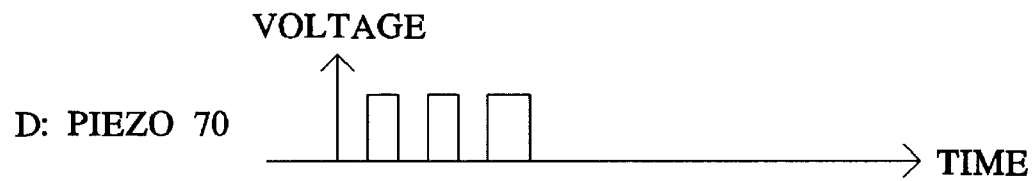
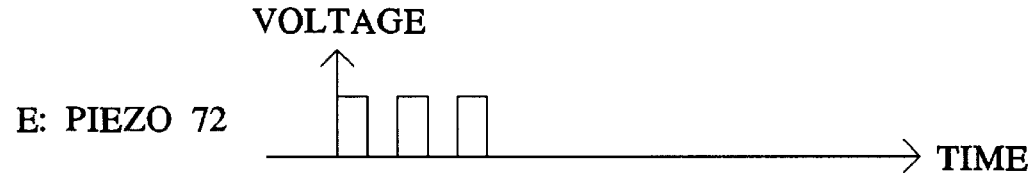
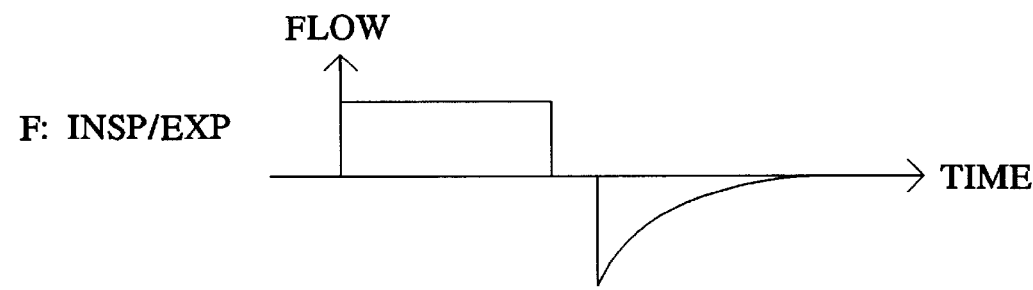

6,032,665

DOSING DEVICE FOR ADDING AN ADDITIVE FLUID TO BREATHING GAS IN AN ANAESTHESIA MACHINE OR VENTILATOR

BACKGROUND OF THE INVENTION

1. Field of the Invention

The present invention relates to a dosing device for adding small amounts of an additive fluid (i.e., a gas or a liquid) to a breathing gas, intended to be supplied to a subject via an inspiratory line in an anaesthetic machine or ventilator during inspiratory phases.

2. Description of the Prior Art

As used herein, the phrase "additive fluid" includes any mixture of gases, diluted or undiluted, as well as pure gases. For instance, NO diluted in $N_2$ can be used as additive gas, pure xenon can used as additive gas. Liquid anaesthetic also can be used as an additive fluid. Vaporized anaesthetic as a (pure or diluted gas) can be used as an additive fluid.

In inhalation anaesthesia, a small amount of anaesthetic is added to breathing gas for inhalation by a subject. The anaesthetic can be supplied to the breathing gas in the form of gas or liquid. When supplied in form of gas, some of the breathing gas is allowed to bubble through or pass across the surface of a liquid anaesthetic in order to vaporize it. The resulting mixture, containing a relatively high concentration of anaesthetic, is then added to the rest of the breathing gas in a controlled fashion. The anaesthetic can also be delivered directly into the breathing gas as a liquid, whereupon it quickly vaporizes. In the latter case, some kind of heating may be necessary in order to avoid cold gas from reaching the subject and to enhance the vaporization of the liquid.

Other substances that can be supplied, preferably near the subject, are NO, surfactant and other therapeutic substances.

Swedish Patent 448 347 describes a method for mixing gases in predetermined proportions and dosing the gas mixture in conjunction with anaesthesia and respirator care. Different gases are pulse-injected into a mixing chamber for mixing in same and subsequent dosing of the gas mixture. The proportions of the different gases are governed by the volumes of the gas pulses.

Accurate dosing of small amounts of gas or liquid in a safe manner is difficult and problematic. Known dosing devices normally operate with relatively large volumes of the additive, from which dosing volume the additive gas/liquid is taken. If a fault occurs in the device, relatively high doses can be taken from the dosing volume. Even if other safety measures for the patient intercede, the patient may still be exposed to quantities that could cause discomfort, and in the worst case even be harmful or lethal.

SUMMARY OF THE INVENTION

An object of the present invention is to provide a dosing device, for gases and/or liquids, which achieves a reliable and exact addition of (in particular) small doses of specific additive gases or a liquid, such as anaesthetic liquid, to a main flow of breathing gas supplied to a subject. The doses to be supplied are small, up to the order of 500 ml/min.

A high degree of safety and reliability with exact dosing are achieved with the dosing device according to the invention. The dosing device is small and can therefore be located close to the subject. Dead space, which prevents the dose from reaching the subject in the desired manner, is avoided. The dosing device has a first valve at an inlet, connected to an intermediate dosing chamber, and a second valve at an outlet. The inlet is connected to a source of additive fluid. The dosing chamber has a volume of a magnitude substantially equal to the volume of the dose to be supplied during one inspiratory phase. Even if the entire dosing volume for some reason should be emptied into the breathing gas, any overdose would be kept low and may not even cause discomfort for the patient. The use of two valves increases safety, especially when they are controlled so that only one valve at a time is open for passing additive gas or liquid.

Dosing can be controlled by controlling the number and duration of the second valve's opening times during inspiration a controlled amount of additive gas or liquid is supplied to the breathing gas from the dosing chamber. By using a dosing chamber slightly larger than the dosage to be delivered during the inspiratory phase, the output pulses of additive gas or liquid will be dispensed at a substantially constant pressure, thereby contributing to exact dosing. For safety reasons, both valves are kept closed when no gas or liquid is to be passed into the dosing chamber or to the breathing gas.

According to one embodiment of the dosing device of the invention, a control unit is arranged to cause operating means to open the first valve first, so as to fill the dosing chamber with gas or liquid under positive pressures thereafter closing the first valve and opening the second valve. Thus, the dosing chamber fills when the first valve opens while the second valve is closed, whereupon the first valve is closed and the second valve is opened for brief, controlled periods of time to inject the desired dosing volume into the main flow. Thus there never is any direct connection between the source of gas or liquid and the patient. The opening of the first valve can be made during the expiratory phases.

This provides for an alternate control to achieve the accurate dosing. By alternately opening and closing the valves during the inspiratory phase. The dosing chamber can be refilled one or several times during the inspiratory phase.

This can also be used when larger doses of the additive gas or liquid is to be supplied. The first and second valves can then alternately be opened and closed during the inspiratory phase. The dosing chamber thus will contain an exact volume at an exact pressure each time the second valve opens during the inspiratory phase and dosing becomes more accurate. in this case, the dosing chamber can be made much smaller than the total dose to be given.

It is also possible to allow both valves to be open simultaneously, in particular if the additive gas or liquid is in no way discomforting or harmful to the patient. Alternately, other precautions for avoiding overdosing can be used such as a diffusion membrane between the dosing device and the breathing gas. The diffusion of gas/liquid through the membrane will then govern the maximum dose that can be supplied to the patient.

Yet another way of accomplishing the dosing is to open the second valve during the dosing period of the inspiratory phase and then to control the dosing by opening and closing the first valve. In such a case, the dosing chamber can be considerably smaller than the dose to be supplied. to another embodiment of the dosing device of the invention, the operating means and formed by piezoelectric elements which, when actuated, are devised to lift a valve body off its valve seat in order to open the valve. This results in a valve which respond rapidly to activation, compared to the response of bimetallic actuators (laminates with different coefficients of linear, thermal expansion) conventionally employed as operating means. In this embodiment, the valve body is also lifted by piezoelectric actuators exerting great force, compared to the force generated when electrostatic actuators as are conventionally employed as operating means. This embodiment of the dosing device according to the invention ensures that the dosing device's valves operate rapidly, and reliably and have a simple design.

In another embodiment of the dosing device in accordance with the invention, the dosing device is devised so the positive pressure of a connected source of gas or liquid acts to close the valve body. The closing and sealing effect of the positive pressure, typically 5 bars, of the source of gas or liquid is a major advantage from a safety point of view.

According to another embodiment of the dosing device in accordance with the invention, the apparatus is made by micromachining silicon. Micromachining silicon (using microelectronic technology) makes it possible to manufacture small, identical dosing devices with high performance distribution of gas or liquid at low cost. This fabrication technology therefore makes mass-manufacturing possible at low cost, so that the dosing device could conceivably be devised as a disposable article.

DESCRIPTION OF THE DRAWINGS

FIG. 3 shows a first set of diagrams illustrating a first possible mode of operating the embodiment in FIG. 2.

FIG. 4 shows a second set of diagrams illustrating a second possible mode of operating the embodiment in FIG. 2.

DESCRIPTION OF THE PREFERRED EMBODIMENTS

Figure 1:
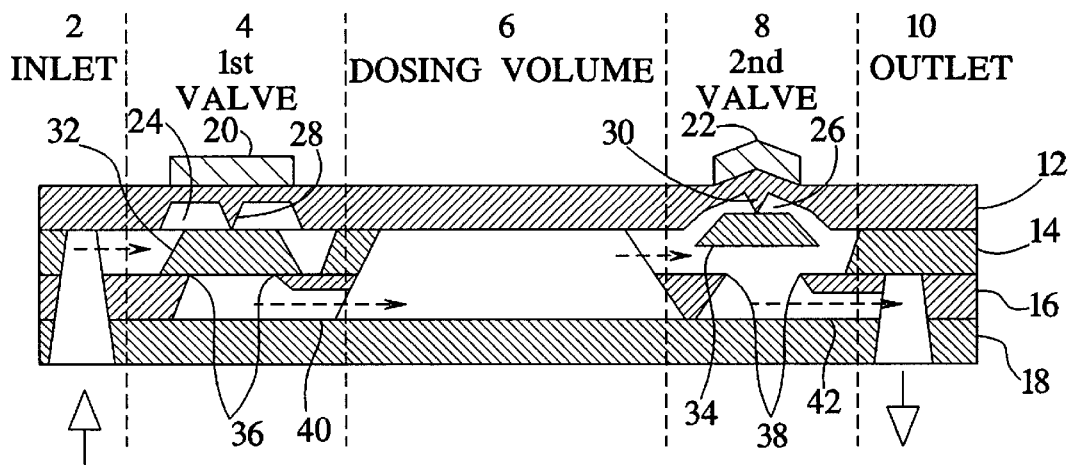
FIG. 1 shows a cross-section of a first embodiment of the dosing device according to the invention.

FIG. 1 shows a cross-section of a first embodiment of the dosing device according to the invention. The dosing device has an inlet 2, a first valve 4, a dosing chamber (dosing volume) 6, a second valve 8 and an outlet 10 laterally arranged on micromachined discs 12, 14, 16 and 18 and possibly glass to which the discs 12, 14, 16 and 18 have been bonded.

Piezoelectric elements 20 and 22 are respectively glued at the regions of the valves 4 and 8 on top of the disc 12. These region valves 4 and 8 respectively have notches 24 and 26 in the disc 12 and central pins 28 and 30 to which valve bodies 32 and 34 are attached. The valve bodies 32 and 34 are set on respective valve seats 36 and 38, arranged in the disc 16.

When a piezoelectric element 22 is activated, it causes the disc 12 to bulge upwardly in its valve area, as illustrated in FIG. 1 for the second valve S. Here, the valve body 34, attached to the central pin 30, is lifted off the associated valve seat 38. The dosing chamber 6 is then coupled to the dosing device's outlet 10 via the channel 42.

The first valve 4 is devised in the same way as the second valve 8 and is shown closed in FIG. 1 with the valve body 32 pressing against its valve seat 36 since the piezoelectric element 20 is not activated. A channel 40 admits additive gas or liquid to the dosing chamber 6 when the first valve 4 is open.

The path of the additive gas or liquid through the dosing device is designated with dashed arrows. The gas/liquid enters the dosing device at the inlet 2, passes through the first valve 4 to the dosing chamber 6 and from the dosing chamber 6, through the second valve 8 to the outlet 10.

Since piezoelectric elements 20 and 22 are used as operating means for the valves 4 and 8, the valves 4 and 8 can be operated rapidly, and the valve bodies 32 and 34 are lifted with relatively great force, also resulting in rapid and reliable valve operation. The response time of the valves is in the order of 1 ms.

For safety reasons, both valves 4 and 8 are normally closed and only open when voltage is applied to the piezoelectric elements 20 and 22. The valve bodies 32 and 34 are also designed so feed pressure exerts a closing and sealing effect on the valves 4 and 8. Since feed pressure is relatively high, as noted above, the valves 4 and 8 should appropriately be pressure balancing, i.e. they should counter-balance the high feed pressure, enabling closed valves to he opened by relatively light force.

The dosing device can be operated as follows:

The first valve 4 is opened by activation of the piezoelectric element 20, and the dosing chamber 6 fills with an additive gas or liquid, such as No or liquid anaesthetic, from a source of gas or liquid at a constant positive pressure, typically 5 bars, connected to the inlet 2. The first valve 4 is then closed, and the second valve 8 is opened for a number of brief, controlled periods of time by corresponding activation of the piezoelectric element 22, so the desired dose of additive gas or liquid is expelled from the dosing chamber 6 and into the outlet 10 which is directly connected to the main flow of breathing gas. The duration and number of pulses determine the total dose.

Allowing only one of the valves 4 or 8 to be opened at a time increases safety for patient, since there is never a direct connection between the gas/liquid source and the patient. Depending on, inter alia, which substance is added and the amount of substance to be added, the valves 4 and 8 may in some instances be operated to be simultaneously open for allowing a larger flow of gas/liquid.

Control of the valves 4 and 8 also depends on the selection of size of the dosage chamber 6. Alternate operations for the first embodiment are discussed in more detail in connection with FIGS. 3–5.

Figure 2:
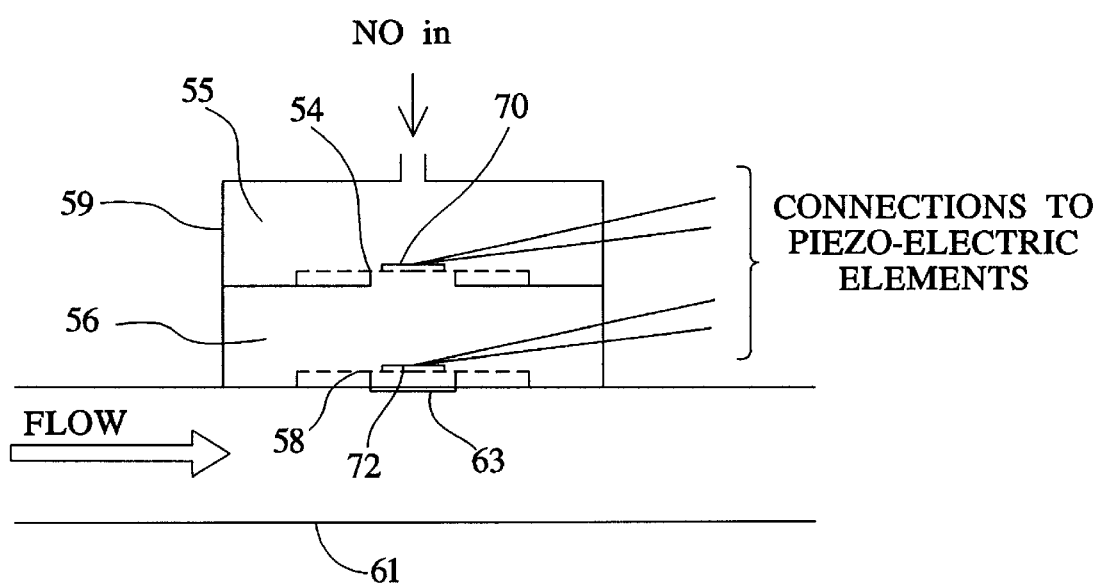
FIG. 2 shows a schematic depiction of a second embodiment of the dosing device according to the invention.

FIG. 2 shows another embodiment of the dosing device according to the invention. In this embodiment, the first valve 54, the dosing chamber 56 and the second valve 58 are arranged in a stack and are fabricated in a silicon housing 59. This embodiment also includes piezoelectric elements 70 and 72 for operating the valves 54 and 58, respectively.

The dosing device's outlet is directly connected to a line 61 carrying the main flow of breathing gas.

A diffusion membrane 63 is in this case arranged as an extra safety precaution at the dosing device's outlet. The purpose of this membrane 63 is to prevent excessively high doses of additive gas or liquid from being injected into the breathing gas if both the valves 54 and 58 are in the open position due to a malfunction. Such extra precaution can be used when therapeutically active substances that are harmful in relatively small doses or substances that may become lethal after chemical reactions are being dosed. One such substance is NO. Several investigations indicate very positive therapeutic effects of NO when given to patients in extremely small doses (less than about 100 ppm). Yet, NO is a harmful gas above a certain concentration, and can even become lethal when it reacts with oxygen and forms $NO_2$.

The embodiment in FIG. 2 indicates that the dosing device in this case is connected to a source of NO.

Upstream from the inlet valve 54, there is a space 55 which is directly connected to the source of additive gas, NO in this embodiment. This space 55 accordingly holds additive gas at the prevailing positive pressure. The space 55 can be viewed as an inlet to the dosing device.

FIG. 3 shows three diagrams as an example of one way of operating the dosing device for dosing the additive gas or liquid. In this case reference is made to the second embodiment in FIG. 2, but the same operation can be applied to the dosing device according to the first embodiment in FIG. 1.

Diagram A shows the chronological sequence for activation of the piezoelectric element 70 for the first valve 54, diagram 3 shows the chronological sequence for activation of the piezoelectric element 72 for the second valve 58 and diagram C shows a respiratory cycle consisting of an inspiratory phase and an expiratory phase.

As this example shows, voltage is applied to the piezoelectric element 70 throughout the inspiratory phase, the first valve 54 being therefore open the whole inspiration time. Three brief voltage pulses are applied to the piezoelectric element 72 of the second valve 58 during the initial part of the inspiratory phase, and three corresponding pulses of additive gas are accordingly injected into the main flow of breathing gas.

In the dosing operation described above, both the inlet valve 54 and the outlet valve 58 are open during the brief pulses. The dosage chamber 56 can therefore be smaller than the dose to be supplied during the inspiratory phase. In fact, the dosing chamber 56 can be much smaller than the dose to be supplied.

As noted above, closing the inlet valve before the outlet valve opens may be preferable from a safety point of view. This operating procedure is obviously even possible with the embodiment in FIG. 2, however, as an additional safety feature to prevent excessively high doses of additive gas, a diffusion membrane 63 can be arranged in the outlet as noted in the embodiment in FIG. 2 above.

FIG. 4 shows three diagrams as a second example of operating the dosing device for dosing. In this case also, reference is made to the second embodiment in FIG. 2, but the same operation can be applied for the dosing device according to the first embodiment in FIG. 1.

Diagram D shows the chronological sequence for activation of the piezoelectric element 70 for the first valve 54, diagram E shows the chronological sequence for activation of the piezoelectric element 72 for the second valve 58 and diagram F shows a respiratory cycle consisting of an inspiratory phase and an expiratory phase.

As this second example shows, voltage is applied to the piezoelectric element 70 at intervals during the inspiratory phase, the first valve 54 therefore being open at these times only for filling the dosing chamber with additive gas. Three voltage pulses are applied to the piezoelectric element 72 of the second valve 58 in-between these openings of the first valve 54, and three corresponding pulses of additive gas are accordingly injected into the main flow of breathing gas.

In this case safety is maximum, since there is no time when gas can flow directly from the source to the flow of breathing gas. The dosing chamber 56 in this case also can have a (considerably) smaller volume than the dose to be supplied.

Figure 5:
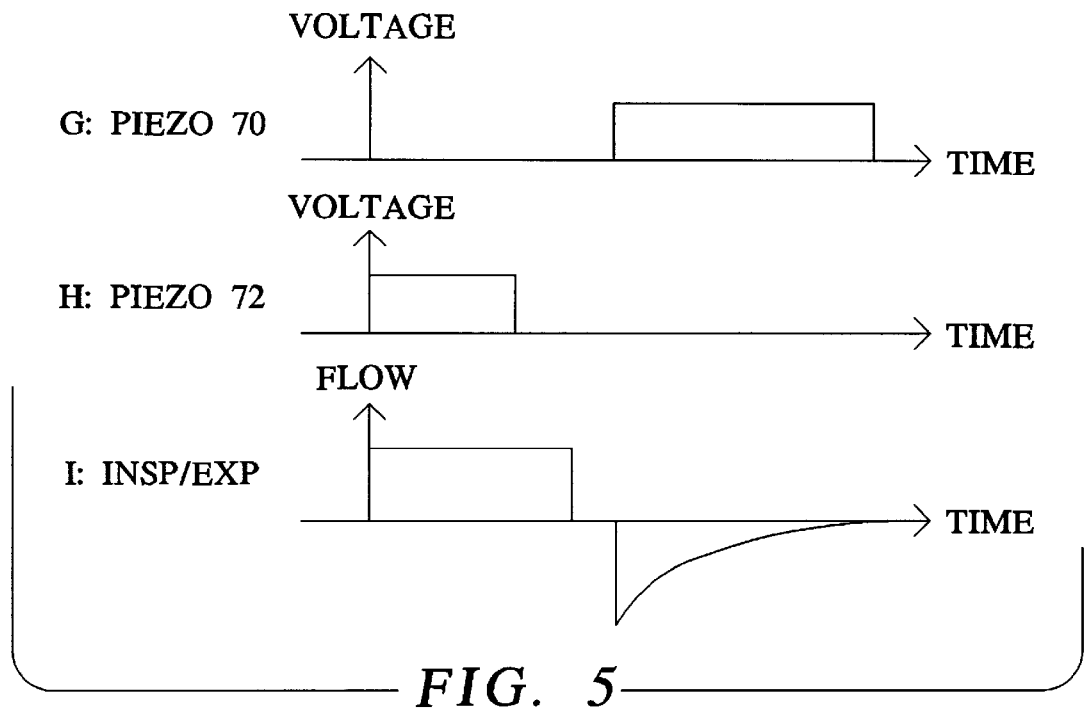
FIG. 5 shows a third set of diagrams illustrating a third possible mode of operating the embodiment in FIG. 1.

FIG. 5 shows three diagrams as a third example of operating the dosing device for dosing. In this case also, reference is made to the second embodiment in FIG. 2, but the same operation can be applied for the dosing device according to the first embodiment in FIG. 1.

Diagram G shows the chronological sequence for activation of the piezoelectric element 70 for the first valve 54, diagram H shows the chronological sequence for activation of the piezoelectric element 72 for the second valve 58 and diagram I shows a respiratory cycle consisting of an inspiratory phase and an expiratory phase.

As this third example shows, voltage is applied to the piezoelectric element 70 during the expiratory phase, the first valve 54 therefore being open during the expiratory phase only for filling the dosing chamber 56 with additive gas. One extended voltage pulse is applied to the piezoelectric element 72 of the second valve 58 during the inspiratory phase, and a corresponding pulse of additive gas is accordingly injected into the main flow of breathing gas.

In this case the dosing chamber 56 should have a somewhat larger volume than the dose to be given. This is particularly preferable if a gas is to be supplied, since pressure in the dosing chamber will decrease as the dose is given. Since the pressure difference is large, however, the dosage can still be controlled with high accuracy.

For all examples given above, the system with two valves and an intermittent dosing chamber provides for a safer dosing device. If one valve cease to operate and is jammed in an open position, dosage can still be performed by the other valve. In the alternative the other valve can effectively close the dosing device and prevent further dosing. The extra dosage supplied in any case can never be more than what is contained in the dosage chamber. Combinations of all three examples of control are possible.

Figure 6:
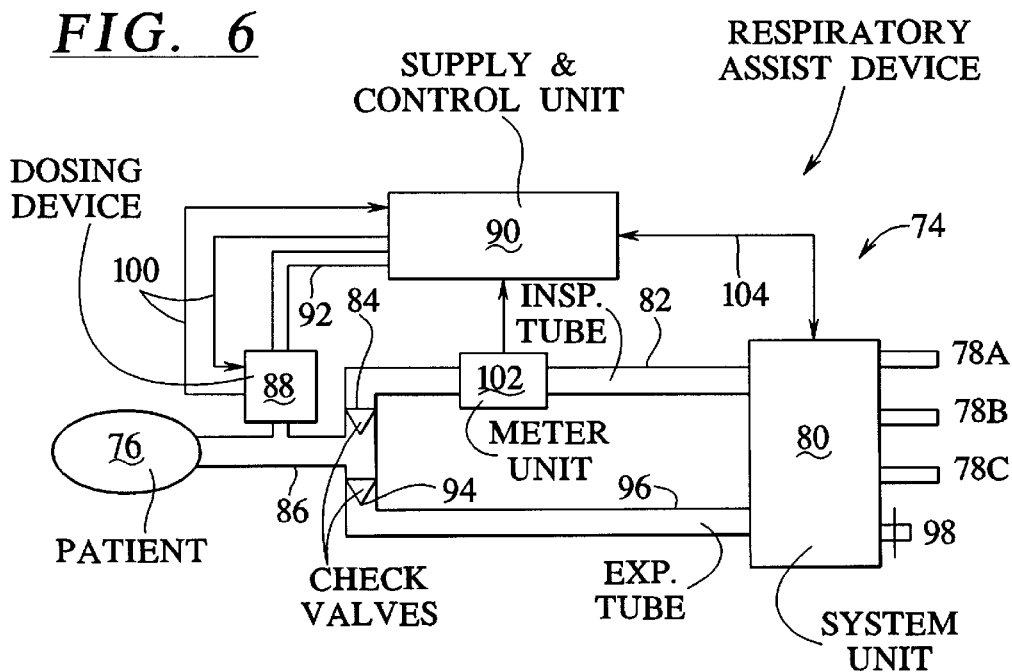
FIG. 6 shows the dosing device connected to a ventilator/anaesthetic machine.

FIG. 6 shows a dosing device 88 according to the invention connected to a respiratory assist device 74, such as a ventilator or an anaesthetic delivery system, for dosing an additive gas or liquid to a breathing gas supplied to a patient 76. The respiratory assist device 74 has a system unit 80 (the configuration of which determines whether the system operates as a ventilator, or an anaesthetic machine), an inspiratory tube 82 with a first check valve 84, a patient tube 86 and an expiratory tube 96 with a second check valve 94. The inspiratory tube 82 and the patient tube 86 together form the inspiratory line. The system unit 80 includes gas connections 78A, 78B and 78C for connecting the gas(es) that form the breathing gas and an evacuation connection 98 for evacuating breathing gas from the expiratory tube 96.

When the system unit 80 is a ventilator, all gas in the expiratory line 96 is evacuated. When the system unit 80 is an anaesthetic machine, more or less of the expired gas can be re-circulated to the patient 76 according to known principles. Neither the ventilator, nor the anaesthetic machine therefore need be further described here.

The dosing device 88 in this case is connected to the patient tube 86, i. e. as close as possible to the patient 76. The location close to the patient 76 is preferable in many instances since the dosing can be more accurate (the dose of gas or liquid can more reliably reach the target areas in the patient lungs 76) when releasing small doses at selected portions of the inspiratory phase. Dosing to the farthest parts of the lungs in particular can be achieved by dosing at, or immediately prior to, onset of the inspiratory phase. Closeness to patient 76 is also advantageous when dosing unstable substances, such as NO.

The dosing device 88 is connected to a supply and control unit 90 for the additive gas or liquid. The gas/liquid is supplied to the dosing device, preferably under high pressure, via supply tube 92. Signal lines 100 connect the dosing device 88 and the supply and control unit 90. in order to obtain accurate concentrations, a meter unit 102 can be arranged in the inspiratory line 82 for measuring, inter alia, flow and pressure of the breathing gas. Instead of the meter unit 102, or as a complement to this, a signal line 104 between the supply and control unit 90 and the system unit 80 can be used for transferring relevant information between the system unit 80 and the supply and control unit 90. For instance, information regarding flow and pressure of breathing gas generated in the system unit 80 can be transferred to the supply and control unit 90 for control of the dosing device 88.

The supply and control unit 90 can of course be integrated with the system unit 80 in whole or partially. Partial integration can be obtained by integrating all control means into the system unit 80 and having a separate source for the additive gas or liquid connected to the dosing unit 88.

Combinations of the disclosed embodiments can be made where appropriate. In particular a membrane can be used for the first embodiment, or no membrane for the second embodiment. The dosing unit 88 can be placed at any location along the inspiration line, even though it is particularly suitable for the advantageous placement in the immediate proximity to the patient. when dosing anaesthetic, the dosing device 88 could even be integrated with the anaesthetic machine. Several dosing units can be connected in series or in parallel, supplying the same or different additive gases or liquids.

Although modifications and changes may be suggested by those skilled in the art, it is the intention of the inventor to embody within the patent warranted hereon all changes and modifications as reasonably and properly come within the scope of his contribution to the art.

I claim as my invention:

1. A dosing device comprising:
   a connection adapted to place said dosing device in communication with an inspiratory line of a breathing assist device in proximity to a subject;
   a constant-volume dosing chamber having a volume less than or equal to a volume of a dosage to be added to the breathing gas during one inspiratory phase;
   a source of additive fluid;
   an inlet to said dosing chamber and a first valve disposed in said inlet, said inlet connected to said source of additive fluid at a predetermined, constant, positive pressure;
   an outlet from said dosing chamber and communicating with said connection for conveying a dosage consisting exclusively of said additive fluid from said dosing chamber to said connection, and a second valve disposed in said outlet;
   operating means for opening and closing each of said first end second valves; and
   control means for controlling said operating means for opening at least said second valve for at least one interval during said inspiratory phase.

2. A dosing device as claimed in claim 1 wherein said control means comprises means for controlling said operating means for opening said first valve for filling said dosing chamber with additive fluid under positive pressure, for subsequently closing said first valve, and for subsequently opening said second valve.

3. A dosing device as claimed in claim 2 wherein said control means comprises means for controlling said operating means for sequentially opening and closing said first valve and said second valve during said inspiratory phase.

4. A dosing device as claimed in claim 2 wherein said control means comprises means for controlling said operating means for opening said first valve for filling said dosing chamber with additive fluid during an expiratory phase.

5. A dosing device as claimed in claim 1 wherein said control means comprises means for controlling said operating means for opening said first valve for filling said dosing chamber with additive fluid and for simultaneously opening said second valve for supplying a dosage of said additive fluid to said connection.

6. A dosing device as claimed in claim 1 wherein each of said first and second valves comprises a valve seat normally closed by a valve body, and wherein said operating means comprises a first piezoelectric element at said first valve for, when activated, lifting said valve body of said first valve off of the valve seat of said first valve for opening said first valve, and a second piezoelectric element at said second valve for, when activated, lifting said valve body of said second valve off of said valve seat of said second valve for opening said second valve.

7. A dosing device as claimed in claim 1 wherein said first valve has a valve seat normally closed by a valve body by positive pressure, and said dosing device further comprising a source of positive pressure in communication with said valve body.

8. A dosing device as claimed in claim 1 wherein said dosing device is comprised of micromachined silicon.

9. A dosing device as claimed in claim 8 wherein said inlet, said first valve, said dosing chamber, said second valve and said outlet are laterally arranged relative to each other in a plurality of micromachined and bonded silicon discs.

10. A dosing device as claimed in claim 8 wherein said inlet, said first valve, said dosing chamber, said second valve and said outlet are disposed in a stack.

\* \* \* \* \*